United States Patent [19]

McWilliams et al.

[11] Patent Number: 4,721,824

[45] Date of Patent: Jan. 26, 1988

[54] GUARD BED CATALYST FOR ORGANIC CHLORIDE REMOVAL FROM HYDROCARBON FEED

[75] Inventors: John P. McWilliams, Woodbury; Margaret I. Nemet-Mavrodin, Robbinsville; Catherine T. Sigal, Lawrenceville; Robert C. Wilson, Jr., Woodbury, all of N.J.

[73] Assignee: Mobil Oil Corporation, New York, N.Y.

[21] Appl. No.: 23,896

[22] Filed: Mar. 12, 1987

Related U.S. Application Data

[63] Continuation of Ser. No. 908,916, Sep. 18, 1986, abandoned, which is a continuation of Ser. No. 653,275, Sep. 24, 1984, abandoned.

[51] Int. Cl.⁴ .......................... C07C 2/64; C07C 5/22; C10G 17/00
[52] U.S. Cl. .................................. 585/448; 208/262; 585/470; 585/823
[58] Field of Search ...................... 585/448, 470, 823; 208/262

[56] References Cited

U.S. PATENT DOCUMENTS

| | | | |
|---|---|---|---|
| 2,328,707 | 9/1943 | Clar et al. | 208/262 |
| 2,413,871 | 1/1947 | Hepp | 196/36 |
| 2,481,300 | 9/1949 | Engel | 196/36 |
| 2,951,804 | 9/1960 | Juliard | 208/91 |
| 2,967,819 | 1/1961 | Leum et al. | 208/88 |
| 3,278,266 | 10/1966 | Welch et al. | 23/154 |
| 3,898,153 | 8/1976 | Louder et al. | 208/88 |
| 3,935,295 | 1/1976 | La Hue et al. | 423/240 |
| 3,972,832 | 8/1976 | Butter et al. | 252/437 |
| 4,034,053 | 7/1977 | Kaeding et al. | 260/672 |
| 4,127,470 | 11/1978 | Baird, Jr. et al. | 208/58 |
| 4,128,592 | 12/1978 | Kaeding | 260/671 |
| 4,137,195 | 1/1979 | Chu | 252/437 |
| 4,341,745 | 7/1982 | Zopff et al. | 423/210 |

FOREIGN PATENT DOCUMENTS 2079236 2/1971 France .

*Primary Examiner*—Curtis R. Davis
*Attorney, Agent, or Firm*—Alexander J. McKillop; Michael G. Gilman; Malcolm D. Keen

[57] ABSTRACT

A method is provided for removing trace amounts of organic chlorides from feedstocks by passing the feedstock in contact with a guard bed catalyst comprising shaped particles formed by extruding a mixture of magnesium oxide and a binder inert to the feedstock. The process has particular importance in removing organic chlorides from toluene feedstocks prior to contacting toluene with a disproportionation or alkylation catalyst comprising magnesium-ZSM-5.

26 Claims, No Drawings

GUARD BED CATALYST FOR ORGANIC CHLORIDE REMOVAL FROM HYDROCARBON FEED

This is a continuation of application Ser. No. 908,916 filed Sept. 18, 1986, which is a continuation of application Ser. No. 653,275 filed Sept. 24, 1984 both of which are now abandoned.

BACKGROUND OF THE INVENTION

1. Field of the Invention

This invention relates to a method of removing organic chloride contaminants from hydrocarbon feedstocks. In particular, the invention is concerned with a method of protecting metal-containing zeolite catalysts against the deleterious effects of organic chlorides by use of a novel guard bed catalyst.

Hydrocarbons of natural or synthetic origin as generally available are often contaminated by the presence therein of impurities in substantial amounts, the removal of which is essential before such hydrocarbons can be efficiently employed as starting materials in processes of converting such hydrocarbons to move valuable derivatives thereof. In particular, chloride impurities in organically combined form may be of natural origin or have been introduced into the hydrocarbon charge during a chemical treating or processing operation.

The deleterious effects of halogens on catalytic function, in particular, on metal-containing hydrocarbon reforming catalysts is known and attempts have been made to treat the hydrocarbon charge for removal of the halogen components prior to reforming the charge. It has been found, for example, that organic chlorides can have a detrimental effect on the activity of the metal-containing reforming catalysts to such an extent that the catalyst loses its ability to promote the various individual reforming reactions. In addition, the catalyst may lost its ability to promote the desired reforming reactions such that the catalyst loses the desired selectivity for desired products.

Chloride contamination is particularly harmful in processes involving the disproportionation and alkylation of toluene to para-xylene and para-ethyltoluene over ZSM-5 zeolite catalysts which also contain magnesium. Such processes are disclosed in U.S. Pat. Nos. 3,972,832; 4,034,053; 4,128,592; 4,137,195; 4,278,827 and 4,447,666, the entire contents of which are herein incorporated by reference. Chloride contamination of the toluene feedstock can alter the selectivity of the process so as to reduce the production of the more important para isomer.

2. Description of the Prior Art

As stated above, there have been previous attempts to remove organically combined halogens from hydrocarbon charge stocks. For example, U.S. Pat. No. 2,413,871 discloses the removal of organically combined chlorine from hydrocarbons by subjecting the hydrocarbon to the action of a mixture of alumina in a suitably active form such as bauxite and quick lime under conditions such as to effect decomposition of the organic chloride compounds. U.S. Pat. No. 2,481,300 discloses that contaminating amounts of impurities such as organically combined halogen can be removed substantially completely from hydrocarbons by contacting the hydrocarbons with a catalyst comprising active carbon in combination with an alkaline compound of an alkali and/or alkaline earth metal. Alkaline earth metals which are specifically mentioned include calcium, barium, and strontium.

U.S. Pat. No. 2,951,804 discloses a method for the removal of acidic organic contaminants from reforming chargestocks by contacting the chargestock with an activated alumina having impregnated thereon an added base such as the hydroxides of alkali metals and alkaline earth metals, the preferred bases being the hydroxide of either sodium or potassium.

U.S. Pat. No. 2,967,819 also discloses a method for protecting hydrocarbon reforming catalysts against the deleterious effect of halogen compounds by contacting the hydrocarbon charge with certain alkaline earth metal compounds prior to contacting the charge material with the metal-containing reforming catalyst. The charge is contacted with alkaline earth metal compounds such as calcium oxide, calcium sulfide, barium oxide, or barium sulfide or mixtures of two or more of these compounds. The compounds or mixture thereof are in the form of solid pellets or granules. In order to provide mechanical strength to the alkaline earth metal compound pellets, such compounds may be mixed prior to pelleting with an inert material such as alumina or magnesia.

U.S. Pat. No. 3,278,266 discloses the separation of hydrogen halides from hydrocarbons by contacting the hydrocarbon charge with a diacid base deposited on a highly porous acid resistant support. Suitable diacid bases include magnesium, calcium, strontium, and barium in the form of their respective oxides or hydroxides. Generally, the alkaline earth base or the diacid base deposit will be between 5 to 20% by weight although amounts as high as 35% and as low as 1% may be used.

U.S. Pat. No. 3,898,153 discloses as a chloride scavenger the use of a caustic solution or a copper guard catalyst.

U.S. Pat. No. 3,935,295 discloses a process for removing hydrogen chloride from a hydrocarbon stream by passing the hydrocarbon stream through a bed of dried and discrete absorbent particles consisting essentially of zinc oxide, a basic compound of calcium and an inert binder.

U.S. Pat. No. 4,127,470 discloses a process of removing sulfur compounds from hydrocarbon feedstocks by contacting the feed with an alkali metal or alkaline earth metal including calcium, barium and magnesium oxides. Suitable supports can be employed such as alumina whereby the supported systems can be prepared by individually impregnating the support which is to be utilized with each reagent. Preferably, the alkaline earth metal compound is utilized as a support for the alkali metal compounds.

U.S. Pat. No. 4,341,745 discloses the removal of acid gases from waste gases by contacting the gases with an absorbent which is a direct reaction product from a mixture of red mud and an alkaline earth metal hydroxide or aluminum oxide. Calcium is the only alkaline earth metal compound specifically disclosed in the patent.

Other methods of dehydrochlorinating (HCl elmination) are known. Note "Catalytic Reduction of Organic Chlorine Compounds in Hydrogen Stream by 50 percent Ni on Kieselguhr Catalysts", [Mokrousova et al, Kinet-Katal, 16 #3, 796–797 (1975)]; "Dehydrochlorination of Chloroalkanes on Solid Acids and Bases" [Mochida et al. *J. Cat.* 43 (1976); *J. Org. Chem.*, 32 (1967), *J. Org. Chem.* 33 (1968)]; and *SRI Report* #102

"Disposal and Recovery of Waste Organo Chlorides" (1976).

SUMMARY OF THE INVENTION

In accordance with the present invention, organic chloride contaminants in hydrocarbon feedstocks are removed prior to processing by contacting the feedstock with a guard bed catalyst of shaped particles comprising magnesium oxide mixed with a suitably inert and extrudable binder. By inert binder in this invention is meant a material which does not alter the composition of the hydrocarbon feedstock.

The use of the guard bed catalyst of the present invention prior to processing the hydrocarbon feedstock eliminates variations in catalyst activity and selectivity that has heretofore been the case when organic chlorides are present and allows relaxation of feed constraints as well as process parameters which required constant adjusting to maintain the quantitative production of desired products when chloride contamination deleteriously affected catalyst properties.

The guard bed catalyst of the present invention has important use in removing small amounts of organic chloride compounds from toluene feedstocks which are converted to para-xylene or para-ethyltoluene over magnesium-containing ZSM-5 catalysts. Although the chlorine impurities in commercially available toluene are extremely difficult to identify, they are believed to be primarily alkyl chlorides. In one toluene source, 1,1,1-trichloroethane has been identified as a particular chlorine-containing impurity.

As discussed above, alkaline earth metal oxides have known activity for organic chloride removal from hydrocarbon feeds. In particular, calcium oxide has been widely used to effect such removal. It has been found, however, that magnesium oxide when prepared according to this invention is more effective than calcium oxide in removing organic chloride contaminants from hydrocarbon feeds.

One disadvantage of using alkaline earth metal oxides, such as magnesium oxide, as a guard bed catalyst is that such materials are not readily processed into shaped particles having desirable physical characteristics such as adequate attrition resistance. Attrition-resistant particles of a uniform size are necessary to reduce pressure drop and flow distribution problems in a guard bed during operation. The most efficient method of obtaining such particles is by mixing magnesium oxide with a suitable binder prior to processing into shaped particles. Thus, in accordance with this invention, the attrition resistant problems of magnesium oxide particles are overcome by mixing magnesium oxide with an inert binder followed by controlled extrusion into, for example, 1/16-inch diameter cylinders, and subsequent calcination to produce uniform particles of good mechanical strength, relatively high surface area and excellent chloride removal activity. Preparation of catalyst particles in this controlled manner allows reproducible manufacture of a catalyst having the desired physical and catalytic properties.

DETAILED DESCRIPTION OF THE INVENTION

The guard bed catalyst of the present invention is preferably in the form of an extrudate which comprises a binder able to be mixed with the active magnesium oxide adsorbent and extruded or pelletized therewith into the desired particle shape. The magnesium oxide component alone is not readily processed into shaped particles. By combining the magnesium oxide with a binder and forming shaped particles such as by the preferred method of extrusion, uniform particles can be continuously produced. Moreover, the guard bed catalyst in the form of an extrudate contains more magnesia than catalyst particles formed by methods of impregnating a support with a solution containing a magnesium compound and calcining to form the oxide. Thus, a catalyst extrudate can remove the organic chloride contaminants from the hydrocarbon feedstock more readily than impregnated supports. The guard bed catalyst particle of the present invention will contain at least about 50 wt.% magnesia, preferably, will contain over 60 wt.% and, more preferably, at least 70 wt.% of the active organic chloride removing agent. The remainder of the particle will be the binder.

The binder utilized to form the attrition-resistant guard bed catalyst particles must be inert with respect to conversion of the hydrocarbon feed being treated to remove organic chlorides, but the binder may exhibit dechlorination activity. The binder must also be readily extrudable, so that mixtures of magnesium oxide and binder can be extruded into particles of uniform size. The binder must be free of leachable chlorides. Examples of suitable binders include clay, silica, alumina, and silica-alumina. A preferred binder is Attapulgus clay which permits facile extrusions of guard bed catalyst particles containing levels of binder as low as 20 wt.%.

Attapulgite clay is found in the Georgia-Florida area of the United States, in India and in the Soviet Union. Attapulgite clay typically contains from about 70% to about 80% by weight of attapulgite, from about 10% to about 15% by weight of montmorillonite, sepiolite and other clays, from about 4% to about 8% by weight of quartz and from about 1% to about 5% by weight of calcite or dolomite.

Various refined versions of attapulgite clay are available from the Engelhard Minerals and Chemicals Corporation under the trade name of Attapulgus Clay. These refined products are beneficated by thermal activation, milling and screening. Non-clay fractions are removed during refinement such that the refined products may contain up to 85% to 90% by weight attapulgite. A typical chemical analysis for an Attapulgus Clay product would be approximately as follows:

| (Volatile-Free Basis) | |
|---|---|
| Silicon ($SiO_2$) | 68.0% |
| Aluminum ($Al_2O_3$) | 12.0% |
| Magnesium (MgO) | 10.5% |
| Iron ($Fe_2O_3$) | 5.0% |
| Calcium (CaO) | 1.7% |
| Phosphorus ($P_2O_5$) | 1.0% |
| Potassium ($K_2O$) | 1.0% |
| Titanium ($TiO_2$) | 0.7% |
| Trace Elements | 0.1% |
| | 100% |

The guard bed catalyst particles are produced by mulling magnesium oxide with the binder and water and extruding the mixture. The extruded particles are dried and calcined. By this method of forming the guard bed catalyst particles, the particles contain at least about 50 wt.% magnesium oxide and preferably, magnesia levels of at least 70 wt.%. In contrast, methods of forming catalyst particles by impregnating a support with a magnesium salt solution and calcining to yield the action component in the form of an oxide have been found to require multiple applications of the salt solutions and calcinations to provide a magnesium oxide loading of greater than 10%. The method of the present invention comprising intimately mixing the solid magnesium oxide with binder and extruding eliminates the need to work with large volumes of solution and is free of harmful emissions given off during calcination as opposed to the emissions formed by calcination of catalysts containing impregnated magnesium salts. More importantly, by forming the guard bed catalyst particles in accordance with the present invention, high magnesium oxide levels are achieved in a single extrusion. The high levels of active component in the guard bed catalyst particles result in high catalytic activity for the removal of organic chlorides and a high capacity for chloride retention.

The dechlorination of the hydrocarbon feedstock is achieved by contacting the feedstock with a bed of the extruded magnesium oxide/binder particles. Removal of the organic chlorides takes place at a temperature within the range of 350° to about 850° F. and space velocities varying from about 1 to about 35 WHSV. The hydrocarbon stream is preferably in vapor form. Preferably, lower temperatures are utilized such as about 350° to about 600° F. The lower temperatures may necessitate lower space velocities ranging from about 1 to about 8 WHSV. It has been found that the magnesium oxide-containing guard bed catalyst can reduce the chloride content of a hydrocarbon feedstock to less than 1 ppmw and even less than 0.5 ppmw.

The following examples illustrate the present invention but are not to be construed so as to strictly limit the invention.

EXAMPLE 1

Various calcium oxide and magnesium oxide guard bed catalyst particles were formed and used to treat a stream of toluene containing 1,1,1-trichloroethane, which was used as a model organic chloride. Physical properties for the various calcined calcia/clay and magnesia/clay 1/16-inch diameter cylindrical extrudates are shown in Table 1. In all cases the binder was Attapulgus clay. The calcia/clay extrudates exhibited good crush strength averaging 62 pounds/inch and relatively high surface areas averaging 56 $m^2/g$. The magnesia/clay particles as formed in accordance with the present invention exhibited crush strengths of 53 to 63 pounds/inch and surface areas of 29 to 160 $m^2/g$.

The catalyst particles of the present invention containing 70% magnesium oxide and 30% Attapulgas clay were formed by the following procedures:

60 grams of MagChem 700 TM MgO from Martin Marietta Chemicals mixed with 29.7 grams of Attagel and 84 grams of deionized water. Attagel 40 is a specially processed Attapulgus clay prepared by Engelhard. It is 80% solids with an average particle size of 0.14μ. The water was added stepwise to the mixture of clay and magnesium oxide and the mixture was mulled for about 20 minutes. The measured percent solids of the mull mixture was 47%. The mixture was extruded into 1/16-inch diameter cylinders using a one-inch diameter barrel auger extruder. The extruded particles were dried at 250° F. and calcined in air for four hours at a temperature of 1000° F. 800 g of MCB (Matheson Coleman Bell) reagent grade MgO were mixed in a muller with 396 g of Attagel 40. 1220 g of deionized water were then added stepwise to the mixture of MgO and clay. The mixture was mulled 20 minutes and had a percent solids of 46.0%. Extrusion of the mixture into 1/16-inch diameter cylinders were carried out using a 2-inch diameter barrel auger extruder. The extruded particles were dried at 250° F. and calcined in air for four hours at a temperature of 1000° F.

Calcia/clay particles were formed in a similar manner to the magnesia/clay particles. As indicated in Table 1, two types of extruders were used in these preparations: a ram extruder or a 2-inch diameter barrel auger extruder.

TABLE 1

Physical Properties of Alkaline Earth Oxide/Attapulgus Clay Extrudates
1/16 inch diameter cylinders; calcined 4 hr at 1000° F. in air

| Catalyst Composition | (1) 50% CaO/50% Clay, ram extruded | (2) 70% CaO/30% Clay, auger extruded (2 in. barrel) | (3) 70% CaO/30% Clay, auger extruded (2 in. barrel) | (4) 80% CaO/20% Clay, ram extruded | (5) 70% MgO/30% Clay, auger extruded (1 in. barrel) | (6) 70% MgO/30% Clay, auger extruded (2 in. barrel) |
|---|---|---|---|---|---|---|
| % Solids of Extrusion (1000° F.) | 48 | 45 | 47 | 49 | 47 | 46 |
| Crush Strength lbs/in | 62 | 50 | 81 | 53 | 52 | 63 |
| Real Density g/cc | 2.722 | 3.083 | 3.001 | 2.934 | 3.149 | 3.262 |
| Particle Density, g/cc | 0.848 | 0.859 | 0.886 | 1.057 | 0.910 | 0.820 |
| Pore Volume cc/g | 0.812 | 0.839 | 0.795 | 0.605 | 0.781 | 0.913 |
| Ave. Pore Diameter Angstroms | 541 | 589 | 513 | 526 | 1078 | 228 |
| Surface Area $m^2/g$ | 60 | 57 | 62 | 46 | 29 | 160 |

Dechlorination activity was measured for some of the catalysts shown in Table 1. The results are shown in Table 2 as a function of temperature and space velocity.

TABLE 2

Dechlorination Activity of Alkaline Earth
Oxide/Attapulgas Clay Extrudates
Atmospheric Pressure, Toluene Spiked with 1,1,1-trichloroethane

| Catalyst | Temp (°C.) | Toluene WHSV | Cl in[1] Feed (ppmw) | Cl in Toluene Effluent (ppmw)[1] at TOS | | | Avg. Cl Removal (%) |
|---|---|---|---|---|---|---|---|
| | | | | 0.5 hr | 1.0 hr | 1.5 hr | |
| (1) | 440 | 34 | 30 | <1 | <1 | <1 | >97 |
| 50% CaO/50% Clay | 200 | 5 | 30 | <1 | <1 | <1 | >97 |
| (2) | 440 | 34 | 25 | <1 (.7 hr) | <1 (1.3 hr) | <1 (2 hr) | >96 |
| 70% CaO/30% Clay | 200 | 5 | 25 | | 2 | 6 (2 hr) | 84 |
| (3) | 440 | 33 | 32 | 4 | 6 | 6 | 83 |
| 70% CaO/30% Clay | 200 | 5 | 32 | 1 | 1 | 3 | 95 |
| (5) | 440 | 34 | 26 | <0.5 (0.75) | | <0.5 | >98 |
| 70% MgO/30% Clay | 320 | 5 | 26 | — | <0.5 | <0.5 (2 hr) | >98 |
| | 200 | 5 | 26 | — | <0.5 | <0.5 (2 hr) | >98 |
| 100% Clay, 1/32 in | 440 | 34 | 27 | 1 | 4 | 8 | 84 |
| Extrudate | 200 | 5 | 27 | 14 | 18 | 16 | 41 |

| | Temp., °C. | Toluene WHSV | Cl in Feed, ppmw | Cl in Effluent at TOS, ppmw | | | | | | | Average Cl Removal, % |
|---|---|---|---|---|---|---|---|---|---|---|---|
| | | | | 0.75 | 1 | 1.5 | 2 | 2.25 | 3 | 4 | |
| (6) | 200 | 5 | 67 | — | 4 | — | 4 | — | 5 | 7 | 93 |
| 70% MgO/30% Clay | 320 | 5 | 67 | — | 2 | — | <1 | — | <1 | <1 | 98 |
| | 365 | 34 | 73 | 22 | — | 11 | — | 13 | 10 | — | 81 |

[1]Chloride analysis by x-ray fluorescence.

As can be seen from Table 2, the magnesia/clay guard bed catalyst particle is the most active. A run with a 1/32-inch, 100% attapulgas clay extrudate as seen from Table 2 showed some activity for chloride removal at higher temperatures, e.g., 440° C. In all the runs shown in Table 2, toluene conversion was minimal, being of the order of 0.1%.

EXAMPLE 2

Guard bed catalysts formed by impregnating a magnesium salt on a support and calcining to form magnesium oxide were compared with regard to dechlorination activity to the magnesium oxide/clay extrudate formed in Example 1. These guard bed catalysts are shown in Table 3.

TABLE 3

Mg Loading on Chloride Guard Bed Catalysts

| Catalysts | Wt % Mg | No. of Impregnations[1] |
|---|---|---|
| 70% MgO/30% clay extrudate | 42.2 | none |
| MgO on activated alumina beads (5 × 8 mesh) | 3.2 | 1 |
| MgO on activated alumina pebbles (8 × 14 mesh) | 4.9 | 1 |
| MgO on γ alumina extrudate | 4.9 | 1 |

TABLE 3-continued

Mg Loading on Chloride Guard Bed Catalysts

| Catalysts | Wt % Mg | No. of Impregnations[1] |
|---|---|---|
| MgO on silica-alumina beads | 2.4 | 1 |
| MgO on silica extrudates | 14.6 | 2 |

[1]A nearly saturated salt solution of 60 ± 5 wt. % $Mg(NO_3)_2 \cdot 6H_2O$ was used for each impregnation.

Table 4 illustrates the dechlorination activity of some of the magnesium-containing guard bed catalysts shown in Table 3.

TABLE 4

Dechlorination Activity of Mg-Containing Guard Bed Catalysts
Atmospheric Pressure, Toluene Feed

| Catalyst | Temp (C.°) | Toluene WHSV | Cl in Feed (ppmw) | Cl in Effluent at TOS (ppmw) | | | | | |
|---|---|---|---|---|---|---|---|---|---|
| | | | | 0.5 hr | 1.0 hr | | 1.5 hr | 2.0 hr | 3.0 hr | 4.0 hr |
| 70% MgO/30% clay extrudate | 440 | 34 | 26 | — | <0.5 (.75 hr) | <0.5 | — | — | — |
| | 320 | 5 | 26 | — | <0.5 | — | <0.5 | <0.5 | <0.5 |
| | 200 | 5 | 26 | — | <0.5 | — | <0.5 | — | — |
| 4.9% Mg on activated alumina pebbles | 430 | 5 | 22 | — | <2 | — | 4 | <2 | 2 |
| 14.6% Mg on silica extrudates | 440 | 5 | 40 | <1 | <1 | <1 | — | — | — |

As can be seen, even at the lower temperature or higher space velocity, the magnesia/clay extrudates were more active in removing the chlorine from the toluene stream. The increase in dechlorination activity can be attributed to the greater amount of magnesium oxide which is present in the guard bed catalysts particle. It is important to note that the high level of magnesium oxide present in the extruded particle cannot be attained by a single impregnation of a binder material.

We claim:

1. A method of removing substantially all organic chlorides from hydrocarbon feedstocks comprising passing an organic chloride-containing feedstock in contact with catalyst particles at a space velocity from about 1 to about 34 WHSV, wherein said particles are obtained by mixing magnesium oxide with a binder substantially inert with respect to said feedstock and shaping said mixture to produce shaped catalyst particles.

2. The method of claim 1 wherein said shaped particles are formed by mixing said magnesium oxide and said binder and extruding the mixture.

3. The method of claim 1 wherein said shaped particles contain at least about 50 wt.% of said magnesium oxide.

4. The method of claim 1 wherein said shaped particles comprise at least about 70 wt.% of said magnesium oxide.

5. The method of claim 1 wherein said inert binder is selected from the group consisting of clay, silica, alumina, and silica-alumina.

6. The method of claim 1 wherein said binder is Attapulgus clay.

7. The method of claim 1 wherein the removal of organic chlorides takes place at a temperature within the range of 350° to about 850° F.

8. The method of claim 7 wherein said temperature is from about 350° to about 600° F. and said space velocity is about 1 to about 8 WHSV.

9. The method of claim 1 wherein said feedstock comprises toluene.

10. The method of claim 1 wherein said feedstock is converted subsequent to contact with said catalyst over a metal-containing catalyst.

11. In a method of passing an aromatic feedstock in contact with a disproportionation or alkylation catalyst wherein said catalyst is capable of being poisoned by chlorine impurities in said aromatic feedstock, the improvement comprising removing substantially all the chlorine impurities from said feedstock by pretreating said aromatic feedstock, prior to passing same over said catalyst, by contacting said aromatic feedstock with a guard bed of catalyst particles having dechlorination activity.

12. The improvement of claim 11 wherein said disproportionation or alkylation catalyst comprises ZSM-5 containing a magnesium component.

13. The improvement of claim 12 wherein said aromatic feedstock comprises at least 50% by weight of one or more compounds selected from the group consisting of benzene, monoalkylbenzene, dialkylbenzene, and trialkylbenzene, wherein the alkyl constituents of said alkylbenzenes contain from 1 to 6 carbon atoms.

14. The improvement of claim 13 wherein said aromatic feedstock comprises toluene.

15. The improvement of claim 11, wherein said guard bed of catalyst particles comprised shaped particles formed by mixing magnesium oxide with a binder inert to said feedstock.

16. The method of claim 15 wherein said shaped particles are formed by extruding a mixture of magnesium oxide and said inert binder.

17. The improvement of claim 15 wherein said shaped particles comprise at least about 50 wt.% of said magnesium oxide.

18. The improvement of claim 15 wherein said shaped particles comprise at least about 70 wt.% of said magnesium oxide.

19. The improvement of claim 15 wherein said inert binder comprises Attapulgus clay.

20. The improvement of claim 11 wherein said feedstock is contacted with said guard bed catalyst particles at a temperature within the range of about 350° to about 850° F. and a space velocity of about 1 to about 34 WHSV.

21. The method of claim 1, wherein said passing step comprises passing feedstock in vapor form.

22. The method of claim 11, wherein said contacting step comprises contacting said feedstock in vapor form.

23. The method of claim 16, further comprises the steps of drying the extruded particle at about 250° F. and calcining the particles in air at about 1000° F.

24. The method of claim 23, wherein the calcining step is maintained for about 4 hours.

25. The method of claim 24, including obtaining calcined particles exhibiting a crushing strength of from about 53 to about 63 pounds/inch.

26. The method of claim 24, including obtaining calcined particles having a surface area of from about 29 to about 160 m$^2$/g.

* * * * *